United States Patent [19]
Schmidt

[11] Patent Number: 5,945,424
[45] Date of Patent: Aug. 31, 1999

[54] TREATMENT OF PERIODIC LIMB MOVEMENT SYNDROME

[75] Inventor: Helmut S. Schmidt, Powell, Ohio

[73] Assignee: G & H Associates, Inc., Columbus, Ohio

[21] Appl. No.: 09/126,819

[22] Filed: Jul. 31, 1998

[51] Int. Cl.$^6$ .......................... A01N 43/90; A01N 37/12; A01N 37/44; A61K 31/52

[52] U.S. Cl. .......................... 514/264; 514/263; 514/565; 424/464; 424/468

[58] Field of Search ...................................... 514/565, 263, 514/264; 424/464, 468

[56] References Cited

FOREIGN PATENT DOCUMENTS

253490 A1   1/1988   European Pat. Off. .
2423529    12/1974   Germany .

*Primary Examiner*—Frederick Krass
*Attorney, Agent, or Firm*—Mueller and Smith, LPA

[57] ABSTRACT

The present invention is directed to a method for treating patients afflicted with periodic limb movement syndrome (PLMS) which includes administering to said patient prior to sleep a combination of: carbidopa and levodopa in 25 and 100 mg quantities, respectively, and carbidopa and levodopa in 25 and 200 mg quantities, respectively, in sustained release form. The sustained-release carbidopa and levodopa preferably is supplied in a tablet contained 50 mg of carbidopa and 200 mg of levodopa. Caffeine may be administered to the patients following sleep.

4 Claims, No Drawings

TREATMENT OF PERIODIC LIMB MOVEMENT SYNDROME

CROSS-REFERENCE TO RELATED APPLICATIONS

None

STATEMENT REGARDING FEDERALLY SPONSORED RESEARCH

Not applicable.

BACKGROUND OF THE INVENTION

Restless Legs Syndrome (RLS) is best described as irresistible leg movements often accompanied by a creeping sensation deep in the limbs. Its is reported to be the fourth leading cause of insomnia after psychiatric disorders, drug abuse, and sleep apneas. Brodeur, et al., "Treatment of restless legs syndrome and periodic movements during sleep with L-dopa: A double-blind, controlled study", *Neurology*, 38, 1845 (December 1988). Bedtime is a major problem for these patients since rest, particularly lying down in bed, is associated with increased dysesthesia and irresistible leg movements, which interfere with sleep onset. Most frequently, the patients move their legs vigorously, flexing, stretching, and crossing them one over the other. The intensity of muscular jerks can vary greatly from one case to another. Often, patients have to get out of bed several times a night.

Nearly all patients with RLS also experience stereotyped, repetitive movements once asleep, a condition known as periodic movements during sleep or periodic limb movement syndrome (PLMS). Periodic movements during sleep represent a distinct nosological entity from RLS. Independent PLMS occurs along with a wide range of sleep-wake complaints, including early sleep onset difficulty, nocturnal awakenings, and daytime sleepiness. See Kryger, et al., "Principles and Practice of Sleep Medicine", 1989, Saunders Company, Chapter 43; Culpepper, et al., "Time of Night Patterns in PLMS Activity", *Sleep*, 15(4):306–311; .Shahal, et al., "Cyclic Leg EMG Activity During NREM-REM Sleep in Patients with Period Leg Movements in Sleep", *Sleep Research???*; Valencia, et al., "Incidence of Sleep Apnea and Nocturnal Myoclonus Among Elderly Females in a Mexican Population", *Sleep Research*, 1990, 19:303; Becker, et al., "Reliability of Bedpartner's Reports for Symptoms of Sleep Apnea and Periodic Leg Movements", *Sleep Research*, 1990:19:188; Sandyk, et al., "Serotonin in Involuntary Movement Disorders", Int. J. Neuroscience, 1988; 42–43; Kotagal, et al., "Relationship of EEG Changes to Periodic Leg Movements", *Sleep Research*, 1990; 19:244; Shafor, et al., "Lumbo-Sacral Spine Abnormalities and Periodic Leg Movements in Sleep", *Sleep Research*, 1990:19:292; Shahal, et al., "Cyclic Leg EMG Activity During NREM-REM Sleep", *Sleep Research*, 1990:19:130

Treatment of RLS and PLMS has varied and includes clonazepam and other benzodiazepines, propoxyphene and other opiates, and L-dopa and other dopoaminergic drugs, for example. See Montplaisir, et al., "The Treatment of Restless Leg Syndrome With or without Periodic Leg Movements in Sleep", *Sleep*, 15(5):391–395 (1992) and Kryger, et al., supra; Bonnet, et al., "The Use of Triazolam in Older Patients With Periodic Leg Movements, Fragmented Sleep, and Daytime Sleepiness", *Journal of Gerontology*: Medical Sciences, 1990, Vol. 45, No. 4, M139–144; Scrima, et al., "Gamma-Hydroxybutyrate Effect on Nocturnal Myoclonus: A Double-Blind Study", *Sleep Research*, 1990; 19:289; Bamford, et al., "Letter Failure of Clonidine to Ameliorate the Symptoms of Restless Legs Syndrome", *Sleep*, 10(4) :398–399 (1987); Guilleminault, et al., "Periodic leg movement, sleep fragmentation and central sleep apnea in two cases: reduction with Clonazepam", *Dur. Respir. J.*, 1988, 1, 762–765. Further on the use of L-dopa can be found in the following publications: Brodeur, et al., supra; Guilleminault, et al., "Periodic Leg Movement, L-Dopa, 5-Hydroxytryptophan, and L-Tryptophan", *Sleep*, 10(4) :393–397 (1987).

While L-dopa has been used somewhat successfully in the treatment of PLMS, often-repeated dosages over the course of the night are required. Dosages effective in the treatment of PLMS also can lead to daytime drowsiness in some patients. The sustained-release form of carbidopa-levodopa was thought to be the answer to repeated nighttime dosages; however, this has not been borne out in clinical studies. Thus, a new regimen is needed in order to deal effectively with patients afflicted with PLMS.

BRIEF SUMMARY OF THE INVENTION

The present invention is directed to a method for treating patients afflicted with periodic limb movement syndrome (PLMS) which includes administering to said patient prior to sleep a combination of: carbidopa and levodopa in 25 and 100 mg quantities, respectively, and carbidopa and levodopa in 25 and 100 mg quantities, respectively, in sustained release form. The sustained-release carbidopa and levodopa preferably is supplied in a tablet contained 50 mg of carbidopa and 200 mg of levodopa. Caffeine may be administered to patients following sleep as it has been observed clinically that caffeine can serve to mitigate some of the spillover effects of carbidopa and levodopa.

DETAILED DESCRIPTION OF THE INVENTION

Sinemet® CR (Merck & Co., Inc.) is a sustained-release tablet containing a 1:4 weight ratio of carbidopa and levodopa (Sinemet® CR 50–200 contains 50 mg of carbidopa and 200 mg of levodopa; Sinemet® CR 25–100 contains 25 mg of carbidopa and 100 mg of levodopa). Other ingredients in Sinemet® CR 50–200 are D&C Yellow 10, magnesium stearate, iron oxide, and a drug delivery system that controls the release of carbidopa and levodopa as it slowly erodes (about 4–6 hours). Carbidopa, an inhibitor of aromatic amino acid decarboxylation, is a white, crystalline compound, slightly soluble in water, with a molecular weight of 244.3. It is designated chemically as (−)-L-α-hydrazino-α-methyl-β-(3,4-dihydroxybenzene) propanoic acid monohydrate. Its empirical formula is $Co_{10}H_{14}N_2O_4 \cdot H_2 0$. Levodopa, an aromatic amino acid, is a white, crystalline compound, slightly soluble in water, with a molecular weight of 197.2. It is designated chemically as (−)-L-β-amino-β-(3,4-dihydroxybenzene) propanoic acid. Its empirical formula is $C_9H_{11}NO_4$. The non-sustained-released form of Sinemet® (often called the "fast acting" form) is supplied in three strengths: 25–100, 10–100, 25–250, carbidopa-levodopa, respectively (mg). Its inert ingredients are reported to include cellulose, magnesium stearate, and starch. Colorants also are added to the tablets in order to be able to distinguish between the three strengths of the drug. Heretofore, this drug combination is prescribed to relieve symptoms of Parkinson's disease.

Use of standard (fast-acting) carbidopa-levodopa to treat PLMS does moderate PLMS in patients that are administered the drug combination prior to sleep. However, studies have revealed that multiple doses over the course of the night often are needed in order for the drug's affect to be sustained. The sustained-release form of carbidopa-levodopa was thought to alleviate the need for subsequent night administrations; however, the drug's effectiveness still leaves a lot to be desired.

Unexpectedly, it has been discovered that a combination of carbidopa-levodopa and sustained-released carbidopa-levodopa dramatically improves the drug's effectiveness in treating PLMS while obviating the need for subsequent doses of the drug during the night. The reason for such improvement in the drug's effectiveness is not totally understood.

Yet, when a simple combination of the drugs is administered, say carbidopa-levodopa (25 mg–100 mg, respectively) and sustained-release carbidopa-levodopa (25 mg–100 mg, respectively), dramatic improvements in PLMS is seen. As the data will demonstrate, the novel dosage regimen of carbidopa-levodopa resulted in an almost three-fold improvement in PLMS compared to conventional carbidopa-levodopa and a two and one-quarter-fold improvement in PLMS compared to sustained-release carbidopa-levodopa.

There are spillover effects from the administration of carbidopa and levodopa in the treatment of RLS/PLMS. It has been observed clinically that caffeine may be administered in small doses (e.g., 50–100 mg) to patients following sleep to mitigate some of the spill over effects of carbidopa and levodopa.

The following example shows how the present invention has been practiced. It should not be construed as limiting the present invention. In this application, all citations are expressly incorporated herein be reference.

EXAMPLE

A study of the effect of three different techniques for using carbidopa-levodopa combination (Sinemet® tablets) to reduce PLMS was undertaken. Detailed scoring of two consecutive night polysomnaographic sleep studies were employed for each patient. The patient received no medication for the first night and one of the three different drug regimens for the second night. The OSMI Standard Method of scoring the "Total Number of Movements" from continuous polysomnographic records of a full night's sleep was employed to evaluate the drug regimens evaluated. This method is based on Richard Coleman's "Periodic Movements in Sleep (Nocturnal Myoclonus) and Restless Leg Syndrome" published in *Sleep and Waking Disorders: Indications and Techniques*, C. Guilleminault, Editor, Butterworths Publishing Co., Boston, Mass., pp. 265–295 (1982), the disclosure of which is expressly incorporated herein by reference. The criteria in the OSMI Method are:

1. The person must be asleep.
2. A movement is scored when it occurs as part of a series of 4 consecutive movements that are separated by at least 4, but not more than, 90 seconds. In most instances, however, the movements should be separated by about 20–40 seconds.
3. The duration of the movements should be between 0.5 and 5 seconds.
4. The amplitude of the movements should be at east one-half the pen deflection of the leg EMG recorded in the pre-sleep testing period (patient calibration).
5. Scoring for the total number of movements—Isolated (i.e., non-successive) movements are not counted. Movements occurring synchronously in both legs (with 4 seconds) are counted as one movement).

The three groups of patients were drawn from historical OSMI recordings of patients that had:

1. polysomnaographic sleep studies recorded for two successive nights.
2. been given Sinemet® the second night and had not been given other medications or used a C-PAP machine.

The 3 groups of patients received the following drug regimen (Night 2):

Group A: 7 patients who received standard Sinemet® 25–100.

Group B: 6 patients who received sustained-release Sinemet® 50–200.

Group C: 6 patients who received a combination of Sinemet® 25–100 and one-half dose of sustained-release Sinemet® 50–200.

The following data were recorded:

TABLE 1

Number of Periodic Limb Movements

| Group A | FAST ACTING | | | | | | | Group |
|---|---|---|---|---|---|---|---|---|
| Patient No. | A1 | A2 | A3 | A4 | A5 | A6 | A7 | Average |
| Night 1 | 34 | 43 | 80 | 110 | 154 | 197 | 211 | 118.4 |
| Night 2 | 43 | 24 | 59 | 100 | 82 | 121 | 184 | 87.6 |
| Absolute Change | −9 | 19 | 21 | 10 | 72 | 76 | 27 | 30.9 |
| % Change | 26.5 | −44.2 | −26.3 | −9.1 | −46.8 | −38.6 | −12.8 | −26.1 |

| Group B | SUSTAINED RELEASE | | | | | | Group |
|---|---|---|---|---|---|---|---|
| Patient No. | B1 | B2 | B3 | B4 | B5 | B6 | Average |
| Night 1 | 221 | 153 | 230 | 31 | 320 | 396 | 225.2 |
| Night 2 | 77 | 81 | 112 | 0 | 206 | 408 | 147.3 |
| Absolute Change | 144 | 72 | 118 | 31 | 114 | −12 | 77.8 |
| % Change | −65.2 | −47.1 | 51.3 | −100.0 | −35.6 | 3.0 | −34.6 |

| Group C | INVENTIVE FORMULATION | | | | | | Group |
|---|---|---|---|---|---|---|---|
| Patient No. | C1 | C2 | C3 | C4 | C5 | C6 | Average |
| Night 1 | 23 | 46 | 103 | 137 | 208 | 287 | 134.0 |
| Night 2 | 17 | 0 | 13 | 52 | 46 | 51 | 29.8 |
| Absolute Change | 6 | 46 | 90 | 85 | 162 | 236 | 104.2 |
| % Change | −26.1 | −100.0 | −87.4 | −62.0 | −77.9 | −82.2 | −77.7 |

In summary, the fast-acting Sinemet® test group revealed a 26.1% decrease in PLMS; the sustained-release Sinemet® test group revealed a 34.6% decrease in PLMS; and the inventive test group revealed a 77.7% decrease in PLMS. Thus, the inventive method was about 3 times more effective than standard Sinemet® and more than twice as effective as sustained-release Sinemet®. This data amply demonstrates the efficacy of the present invention and the unexpected results achieved by the present invention.

I claim:

1. A method for treating patients afflicted with periodic limb movement syndrome (PLMS), which comprises administering to said patients prior to sleep a combination of:
   (a) carbidopa and levodopa in 25 and 100 mg quantities, respectively, in non-sustained release form and
   (b) carbidopa and levodopa in one or more of 25 and 100 mg or 50 and 200 mg quantities, respectively, in sustained release form.

2. The method of claim 1, wherein said carbidopa and levodopa (b) are supplied in a tablet containing 50 mg of carbidopa and 200 mg of levodopa.

3. The method of claim 1, wherein caffeine is administered to said patients following sleep.

4. The method of claim 3, wherein caffeine is administered in a dose of about 50–100 mg.

* * * * *